US006982162B2

United States Patent
Berens et al.

(10) Patent No.: US 6,982,162 B2
(45) Date of Patent: Jan. 3, 2006

(54) CORYNEBACTERIUM GLUTAMICUM STRAIN WITH ENHANCED SECRETION ACTIVITY

(75) Inventors: Stephan Berens, Bielefeld (DE); Jörn Kalinowski, Bielefeld (DE); Alfred Pühler, Bielefeld (DE)

(73) Assignee: Degussa AG, Dusselforf (DE)

( * ) Notice: Subject to any disclaimer, the term of this patent is extended or adjusted under 35 U.S.C. 154(b) by 422 days.

(21) Appl. No.: 09/852,053

(22) Filed: May 10, 2001

(65) Prior Publication Data

US 2002/0055141 A1 May 9, 2002

(30) Foreign Application Priority Data

Dec. 5, 2000 (EP) .......................................... 00110021

(51) Int. Cl.
*C12P 21/06* (2006.01)
*C12N 1/20* (2006.01)
*C12N 1/00* (2006.01)
*C07K 1/00* (2006.01)
*C07H 21/02* (2006.01)

(52) U.S. Cl. ................... 435/252.32; 435/69.1; 435/252.3; 435/320.1; 530/350; 536/23.1

(58) Field of Classification Search ................ 435/69.1, 435/252.3, 252.32, 320.1; 530/350; 536/23.1
See application file for complete search history.

(56) References Cited

FOREIGN PATENT DOCUMENTS

| EP | 0 108 790 | 6/2001 |
|---|---|---|
| WO | WO 88 09821 | 12/1988 |
| WO | WO 01 00 804 | 1/2001 |

OTHER PUBLICATIONS

Billman–Jacobe et al. Applied and Environmental Microbiology (1994), 60(5), 1641–5.*
Van Mellaert et al. Recent Research Developments in Microbiology (1999), 3(Pt. 2), 425–440.*
Attwood et al. Which craft is best in bioinformatics? Comput. Chem. 2001, vol. 25(4), pp. 329–339.*
Ponting, C.P. Issues in predicting protein function from sequence. Brief. Bioinform. Mar. 2001, vol. 2(1), pp. 19–29.*
Smith. Accession U00011. Mar. 1, 1994. (US–09–852–053–3 X U00011).*
Smith. Accession U00011. Mar. 1, 1994. (US–09–852–053–4 X U00011).*
Salim et al., "Heterologous expression of the *Mycobacterium tuberculosis* gene encoding antigen 85A in *Corynebacterium glutamicum*", Applied and Environmental Microbiology, vol. 63, No. 11, 1997, p. 4392–4400.
Billman–Jacobe et al., "Expression and Secretion of heterologous proteases by *Corynebacterium glutamicum*", Applied and Evironmental Microbiology, vol. 61, No. 4, 1995, p. 1610–1613.
Pogliano et al., "SecD and SecF facilitate protein export in *Escherichia coli*", Embo Journal, vol. 13, No. 3, 1994, p. 554–561.
Database EMBL Acc No. Z77724, 1996 XP002154142.

* cited by examiner

*Primary Examiner*—Manjunath Rao
*Assistant Examiner*—Christian L. Fronda
(74) *Attorney, Agent, or Firm*—Pillsbury Winthrop Shaw Pittman

(57) ABSTRACT

The present invention refers to a *Corynebacterium glutamicum* bacterial strain which new isolated and identified secD and/or secF gene(s) is/are genetically modified in a way that secretion of the bacterial strain is enhanced, the protein- and polynucleotide sequences of these genes, a plasmid containing at least one of these genes and the use of such a bacterial strain for production of a desired substance or in a reporter system.

20 Claims, 8 Drawing Sheets

CORYNEBACTERIUM GLUTAMICUM STRAIN WITH ENHANCED SECRETION ACTIVITY

The present invention refers to a bacterial strain of *Corynebacterium glutamicum*, which natural genes secD and secF are identified, isolated and sequenced for the first time, to genetical modification(s) of these new genes, concerning gene sequences as well as gene expression and the use of such genetically modified bacterial strain for production of desired substances as well as in a reporter system for protein translocation.

Protein export across the bacterial cytoplasmic membrane mainly follows the ubiquitous general secretory pathway (GSP). The protein translocation is catalyzed by a set of membrane spanning heterotrimers, consisting of the proteins SecY, SecE and SecG in such a way that three SecYE dimers are assembled around a putative pore. In contrast to SecY and SecE which are essential for cell viability, SecG is apparently not required for the formation of the SecYE ring structure (Economou, A. (1999), Trends in Microbiol. 7, 315–319), but stimulates protein secretion by supporting SecA function (Economou, A, Pogliano, J. A., Beckwith, J., Oliver, D. B. and Wickner, W., (1995), Cell 83, 1171–1181). The essential peripheral membrane protein SecA is the mechanical motor of translocation, a dimeric molecule which binds with its carboxy-terminal end to the SecYEG complex (Economou, A. (1999), Trends in Microbiol. 7, 315–319). Preprotein translocation is driven by cyclic insertion and deinsertion of SecA into the membrane under ATP hydrolysis (Lill, R., Dowhan, W. and Wickner, W., (1990), Cell 60, 259–269) and strongly promoted by the proton motive force across the membrane (Shiozuka, K, Mitzushima, S. and Tokuda, H. (1990), J. Biol. Chem. 264, 18843–18847). The auxiliary translocase subunits SecD and SecF enhances protein export in a different manor: (i) they regulate the membrane cycling of SecA (Duong, F and Wickner, W. (1997), EMBO J. 16, 4871–4879), (ii) they improve the export of proteins with defective signal sequences (Pogliano, J. A. and Beckwith, J., (1994a), EMBO J. 13, 554–561), (iii) they stimulate the proton motive force driven protein translocation (Wickner, W. and Arkowitz, R. A. (1994), EMBO J. 13, 954–953) and (iv) they release mature protein from the membrane (Gardel, C., Johnson, K., Jacq A. and Beckwith, J., (1990), EMBO J. 16, 3209–3216). The chaperone SecB has only been found in gram-negative bacteria so far (Fekkes, P. and Driessen, A., (1999), Microbol. Mol. Biol. Rev. 63, 161–173).

In the gram-positive, non sporulating soil bacterium *Corynebacterium glutamicum*, which is of special interest for the industrial production of fine chemicals (Wohlleben, W., Muth, G. and Kalinowski, J. (1993), Genetic Engineering of Microorganisms, pp. 83–133, edited by A. Pühler, New York, Weinheim), cell wall proteins are the major secretion products (Joliff, G., Mathieu, L., Hahn, V., Bayan, N., Duchiron, F., Renaud, M., Chechter, E. and Leblon, G. (1992), Mol. Microbiol. 6; 2349–2362). Due to this lack of extracellular protease activity and its simultaneous ability to secrete large amounts of proteins, *Corynebacterium glutamicum* is an ideal host for the production of heterologous exoproteins, e.g., as shown for the production of a cellulase from *Cellulomonas fimi* (Paradis, F. W., Warren, R. A. J., Kilburn, D. G. and Miller Jr., R. C., (1987), Gene 61, 199–206), an ovine gamma interferon (Billman-Jacobe, H., Hodgson, A. L. M., Lightowlers, M., Wood, P. R. and Radford, A. J. (1994), Appl Env. Microbiol 60, 1641–1645) and a lipase from *S. hyicus* and a thermonuclease from *S. aureus* (Liebel and Sinskey, U.S. Pat. No. 4,965,197).

Enhancing the secretion of heterologous proteins from *Corynebacterium glutamicum* up to now was only achieved by optimizing the expression of the heterologous protein. Therefore the heterologous protein was fused with a signal sequence of *C. glutamicum* (Liebel and Sinskey, U.S. Pat. No. 4,965,197; Joliff et al., Patent Nr. FR 2,679,922)

Several genes of the GSP have been cloned and sequenced in *Corynebacterium glutamicum*, including secY and secA gene (Kobayashi, M., Fugono, N., Asai, Y., Inui, M., Vertés, A. A., Kurusu, Y. and Yukawa, H. (1994), Gene 139, 99–103; Genetic Analysis and Biomolecular Engineering 15: -13), secG (GenBank D14162), and secE (GenBank AF130462). However, the genes encoding the auxiliary proteins SecD and SecF have not been identified in *Corynebacterium glutamicum*.

Object of the present invention was to provide a means for production of high amounts of desired substances which can be easily isolated from the source of production, as well as a system wherein translocation of the produced proteins can be examined.

This object is met by a genetically modified bacterial strain *Corynebacterium glutamicum* whereby genetical modification concerns at least one of its genes secD and secF.

In all bacterial species analyzed so far sec genes are very conserved in their chromosomal arrangement (Siefert, J. L., Martin, K. A., Abdi, F., Widger, W. R. & Fox, G. E. (1997), J. Mol. Evol. 45: 467–472), particularly secD and secF genes are directly neighboured, e.g. in *Escherichia coli* (Pogliano, J. A. and Beckwith, J., (1994a), EMBO J. 13, 554–561) or *Mycobacterium tuberculosis* (Cole, S. T., Brosch, R., Parkhill, J., Garnier, T., Churcher, C., Harris, D., Gordon, S. V., Eigelmeier, K., Gas, S., Barry, E. E. 3$^{rd}$, Tekaia, F. Badcock, K., Basham, D., Brown, D., et al. (1998), Nature 6685, 537–544).

*Corynebacterium glutamicum* secD has a size of 1911 bp. Homology data and possible Shine-Dalgarno sequence AAGGA suggest that the gene starts with the rare start codon TTG. The gene specifies a protein of 637 amino acids with a calculated molecular mass of 67.689 and a theoretical pI of 4.52. The protein possesses six putative transmembrane spanning regions in an unregular distribution with an extracytoplasmatic loop of 371 residues, predicted by HMMTOP analysis (Tusnády, G. E. and Simon, I., (1998), J. Mol. Biol. 283, 489–506) and six conserved motifs D1–D6, which are present in all known SecD proteins (Bolhuis, A., Broekhuizen, C. P., Sorokin, A., van Roosmalen, M. L., Venema, G., Bron, S., Quax, W. J. and van Dijl, J. M. (1999), J. Biol. Chem. 273, 21217–21224). An alignment of the deduced amino sequences of *Corynebacterium glutamicum* and *M. tuberculosis* SecD (FIG. 2a) revealed 41% identity and an overall similarity of 61% (Myers, G. and Miller, W., (1988) CABIOS 4, 11–17), but the proteins are not homologous over their entire length. Only the C-terminal part with 5 transmembrane regions and the 6 short patterns D1–D6 of corynebacterial SecD are highly conserved, the extracytoplasmatic loop and the elongation of the C-terminus of the protein reveals much lesser conservation to the mycobacterial SecD protein.

*Corynebacterium glutamicum* secF consists of 1209 bp, starts five bases after the secD stop codon and its putative Shine-Dalgarno sequence AGGAG is part of secD 3'end. The distance between the secD stop codon TAG and the secF start ATG is two nucleotides. With 403 amino acid residues the protein shows a calculated molecular mass of 43.664 and a theoretical pI of 5.07. Its structure resembles the SecD protein. It also has six transmembrane spanning regions and an extracytoplasmatic loop of 95 residues but its N-terminus is shorter as compared to the mycobacterial SecF (FIG. 2b). Aligned with *M. tuberculosis* SecF, it exhibits 43% identity and an overall similarity of 60% (Myers, G. and Miller, W., (1988) CABIOS 4, 11–17), but as in the case of SecD, the protein is also not conserved over its entire sequence. Like SecD, only the section containing the transmembrane domains and four regions F1–F4, which are represented in all SecF proteins (Bolhuis, A., Broekhuizen, C. P., Sorokin, A., van Roosmalen, M. L., Venema, G., Bron, S., Quax, W. J. and van Dijl, J. M. (1999), J. Biol. Chem. 273, 21217–21224), are well conserved. Analysis of the SecF amino acid sequence with FingerPRINTscan (Attwood, T. K., Flower, D. R., Lewis, A. P., Mabey, J. E., Morgan, S. R., Scordis, P., Selley, J. and Wright, W. (1999), Nucleic Acid Res. 27, 220–225) revealed two highly conserved possible SecY interaction sites (FIG. 2b), which are part of the transmembrane domains I and VI.

Protein sequence of SecD is shown as SEQ ID NO. 3, encoded by the polynucleotide sequence SEQ ID NO. 1, protein sequence of SeqF is shown as SEQ ID NO. 4, encoded by the polynucleotide sequence SEQ ID NO. 2.

"Substance" in content of the present invention can be any product of a pathway of the bacterium, catabolic as well as metabolic pathway, preferably the "substance" is selected from the group amino acid, oligopeptide, polypeptide and protein. Further the substance can be the product of an introduced heterologous gene or can be produced by this heterologous gene product.

"Homologous protein" or "homologous amino acid sequence" in content with one of the proteins of the present invention means in the present application an amino acid sequence, wherein at least 70%, preferably 80%, more preferably 90% of the amino acids are identical to one of the proteins of the present invention and wherein the replaced amino acids preferably are replaced by homologous amino acids. As "homologous" amino acids are designated which have similar features concerning hydrophobicity, charge, steric features etc.

"Functional mutants" in the sense of the present invention are proteins with an amino acid sequence according to SEQ ID NO. 3 or 4, whereby a single or several amino acids are artificially or naturally replaced by amino acids with different properties, however, the protein as a whole shows similar characteristics concerning e.g. in domains of the three dimensional structure, functional behaviour or effectiveness in one of the embodiments described in the present application.

"Fragments" in the meaning of the present description are polypeptides comprising parts of the amino acid sequence according to SEQ ID NO. 3 or 4 or of a homologous protein or a functional mutant of one of these proteins. Preferably the fragments are functional fragments, which means that they are effectively involved in secreting or in a reporter system described in the present application. Fragments of the protein as well as the whole sequence can further be part of fusion proteins that contain other protein sequences, which foster the level or location of expression or targeting.

To obtain a bacterial strain of *Corynebacterium glutamicum* wherein protein production and/or secretion is enhanced, the genes supporting the production and secretion may be modulated, resulting in a genetically modified bacterial strain according to the invention. "Modification" comprises as well mutation, deletion and insertion of polynucleotides in the genes, as rearrangement of the genes to each other or to their promoters, selection of a suitable promoter, modulating the expression of the proteins, preferably enhancing the expression of secretory proteins, multiplying genes and much further. The modification(s) of the genes supporting the production and secretion of proteins may be located in genes lying in cis or in trans position to each other, modifications may be integrated in the chromosome or may remain on a plasmid.

In one preferred embodiment of the invention at least one of the proteins of the general secretory pathway is overexpressed compared to wild type expression, resulting in an enhanced protein secretion of the bacterium. Preferably, at least one of the proteins SecD and SecF are overexpressed, more preferably these two are overexpressed simultaneously.

Overexpression of the proteins may be obtained for example by setting at least one of the genes secD an/or secF under control of a strong promoter, preferably by inserting the genes in an expression vector which is transferred into the cell or by multiplication of the genes.

Preferably, overexpression of at least one of the proteins SecD and SecF is combined with overexpression of at least one of the essential Sec proteins (SecE, SecY, SecA).

"Overexpression" of a protein means that this protein is expressed to a higher amount than it is naturally expressed from a wild type *Corynebacterium glutamicum*. Preferably overexpression is at least 1.5 fold the amount compared to wild type expression, more preferably at least twofold.

The constructed plasmids for overexpression, containing several combinations of sec genes are shown in Table 1, plasmid maps are shown as FIGS. 3 to 6.

TABLE 1

*Corynebacterium glutamicum* strains and plasmids

| strains/plasmids | relevant genotype | reference |
|---|---|---|
| strains: | | |
| C. g. RES167 | Restriction-deficient mutant of ATCC 13032, Δ(cg1RI- cg1RII) | Universität Bielefeld |
| C .g. INT-D | RES167 secD :: pCR2.1, Km$^R$ RES167 secF :: pCR2.1, Km$^R$ | This study |
| C.g. INT-F | RES167 secG :: cmx. Cm$^R$ RES167 dciAE :: pIAmy2, Tc$^R$, test strain for amylase excretion | This study This study |
| C.g. INT-G | | This study |
| C. g. AMY2 | Vector for cloning of PCR products Ap$^R$, Km$^R$ pK18mob harbouring dciAE fragment | Invitrogen |
| plasmids: | | |
| pCR2.1 | pCR2.1 harbouring secD fragment | Wehmeier et al., (1998) |
| pLW60 | pCR2.1 harbouring secF fragment | This study |
| pInsD | Mobilizable cloning vector, sacB-derivative, Km$^R$ | This study |
| pInsF | pSVB31 containing cmx of pTP10, Cm$^R$ | Schäfer et al. (1994) |
| pK18mobsacB | pK18mob-sacB harbouring secG :: cmx | Universität Bielefeld |
| pEC31 | *E. coli* expression vector, P$_{trc}$, Tc$^R$ *E. coli/C. glutamicum* shuttle expression vector, P$_{trc}$, Km$^R$ | This study |
| pInsG | | Universität Bielefeld |
| pXT99A | *E. coil/C. glutamicum* shuttle expression vector, P$_{trc}$, Tc$^R$ | Universität |

TABLE 1-continued

Corynebacterium glutamicum strains and plasmids

| strains/ plasmids | relevant genotype | reference |
|---|---|---|
| pEC-XK99A | pEC-XT99A harbouring secD downstream $P_{trc}$ | Bielefeld Universität |
| pEC-XT99A | pEC-XT99A harbouring secG downstream $P_{trc}$ | Bielefeld |
| pSecD | pEC-XK99A harbouring secD secF downstream $P_{trc}$ | This study |
| pSecG | | This study |
| pSecDF | pEC-XK99A harbouring secE, secD secF downstream $P_{trc}$ | This study |
| pSecEDF | | This study |
| pSecYDF | pEC-XK99A harbouring secY, secD secF downstream $P_{trc}$ | This study |
| pULMJ95 | E. coil/C. glutamicum shuttle vector, amy, Km$^R$ | Cadenas et al. (1996) |
| pAmy | pEC-XT99A harbouring amy downstream $P_{trc}$ | This study |
| pIAmy2 | pXT99A harbouring amy dciAE-fragment downstream $P_{trc}$ | This study |

One preferred embodiment of the present invention is a *Corynebacterium glutamicum* bacterial strain transformed by plasmid pSecD.

Another preferred embodiment of the present invention is a *Corynebacterium glutamicum* bacterial strain transformed by plasmid pSecDF.

Particularly preferred embodiments of the present invention are *Corynebacterium glutamicum* bacterial strains transformed by plasmid pSecEDF or pSecYDF, respectively.

A bacterial strain according to the invention may contain besides the genetical modification of one of the described sec genes further modifications resulting in enhanced protein secretion. Particularly, a bacterial strain according to the invention contains at least one further heterologous gene, preferably encoding a protein which shall be produced in high amounts. Therefore, the heterologous gene is introduced in a bacterial strain according to the invention—after genetical modification of the sec genes—or an already constructed bacterial strain containing a desired gene is genetically modified concerning the sec genes as described herein.

Introduction of the plasmids used in genetical modification steps may be carried out by any method known in the art, for example by transfection, injection, ballistic missile, viral vectors, electroporation, $CaCl_2$ method or heat shock.

A bacterial strain of the present invention is particularly suitable for amino acid, peptide or protein production, since the produced substances may be secreted from the bacteria in a high amount, and that is why the substances can be isolated directly from medium (supernatant) without cell damage.

A bacterial strain of the present invention may further be used in a reporter system. The reporter system may report about gene regulation, protein expression, protein translocation, or inducibility of gene expression. Preferably in the reporter system the produced proteins are translocated over the cell wall, whereby they are easily to determine in the supernatant.

In one embodiment of such a reporter system protein expression of proteins naturally occurring in *Corynebacterium glutamicum* can be determined by protein characterisation of the secreted proteins.

In another embodiment of a reporter system the bacterial strain of the present invention is transformed by introducing a heterologous marker gene into the cell, encoding a marker protein.

For examining gene regulation the marker gene is located "behind" an interesting promoter, controlling naturally the examined gene. By this construction it is possible to determine how and under which conditions the examined gene is expressed, resulting in conclusions about regulation of this gene.

A similar construction involves further regulating elements of a gene, resulting in a system for determining the inducibility of gene expression of an interesting gene.

In all of the embodiments protein characterization may be carried out by any method known in the art, for example by measuring enzyme activity, SDS-PAGE, sequencing, immunologic methods, i.e. Western blotting, or chromatographic methods.

Protein production by use of a bacterial strain of the present invention can particularly be enhanced by introducing (a) heterologous gene(s) into the bacterial cell enabling the cell to grow faster. Preferably, such a heterologous gene enables the cell to use external energy, normally not used by this bacterial strain. Such external energy comprises several sugars, amino acids, peptides, carbohydrates, fatty acids, organic polymers, inorganic ions and light.

One preferred external energy source is starch. The bacterial strain of the present invention can be transformed in a way that it is able to use starch as a sole energy source, for example by introducing a heterologous amylase gene.

A particularly preferred bacterial strain of the present invention is a *Corynebacterium glutamicum* RES167 strain, transformed by plasmids pSecYDF and pIAmy2.

Amylase secretion of *Corynebacterium glutamicum* AMY2 overexpressing different combinations of sec genes. $1.3 \times 10^6$ cells were incubated for 16 h. Activity in the supernatant was determined 5 times. 1 mU was defined as 1 nmol reducing sugar $min^{-1}$ $ml^{-1}$. A significant increase in amylase secretion could be detected if secD and secF are overexpressed (pSecDF). In *Corynebacterium glutamicum* AMY2/pSecEDF(pSecEDF) and *Corynebacterium glutamicum* AMY2/pSecYDF(pSecYDF) amylase activity is more than doubled compared with *Corynebacterium glutamicum* AMY2(AMY2).

FIG. 2

Growth of different *Corynebacterium glutamicum* strains *Corynebacterium glutamicum* AMY2 (■), *Corynebacterium glutamicum* AMY2/pSecEDF(Δ) and *Corynebacterium glutamicum* AMY2/pSecYDF(●) in minimal medium with starch as sole carbon source. No growth was detectable for *Corynebacterium glutamicum* RES167 (♦). The slight decrease of optical density at the beginning of the curve results from degradation of insoluble parts of starch by the secreted amylase.

Figure 3:
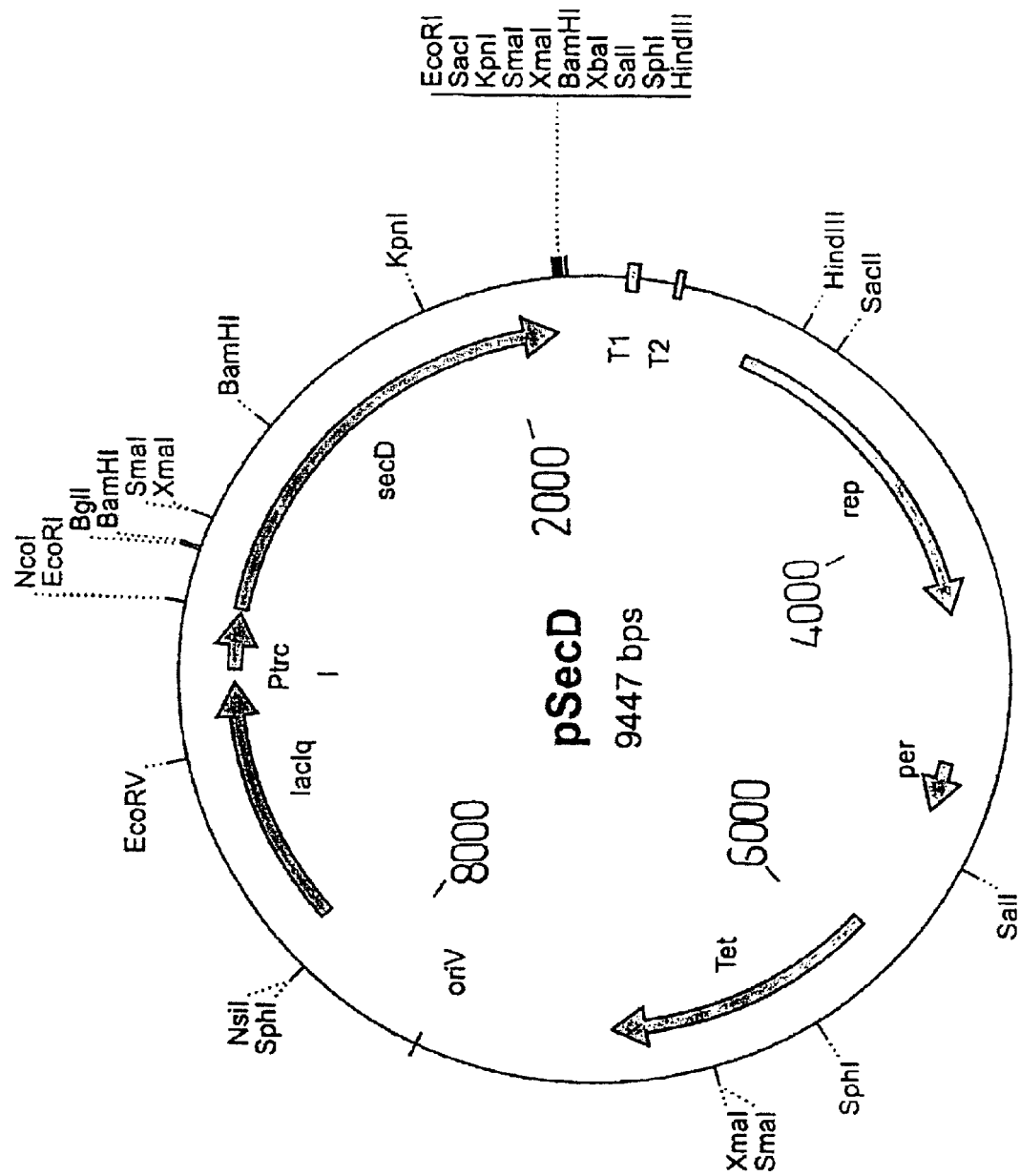
Figure 4:
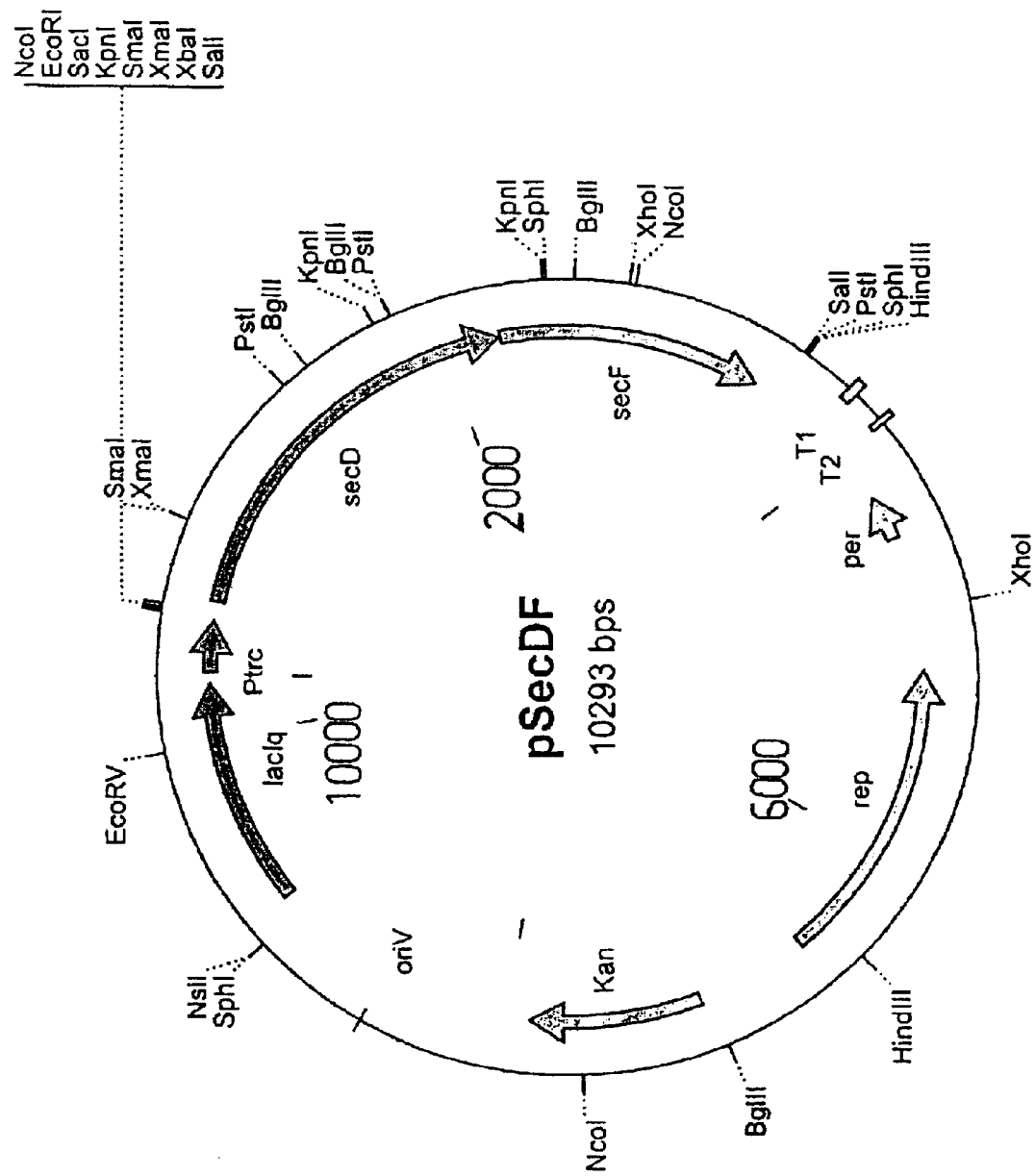
Figure 5:
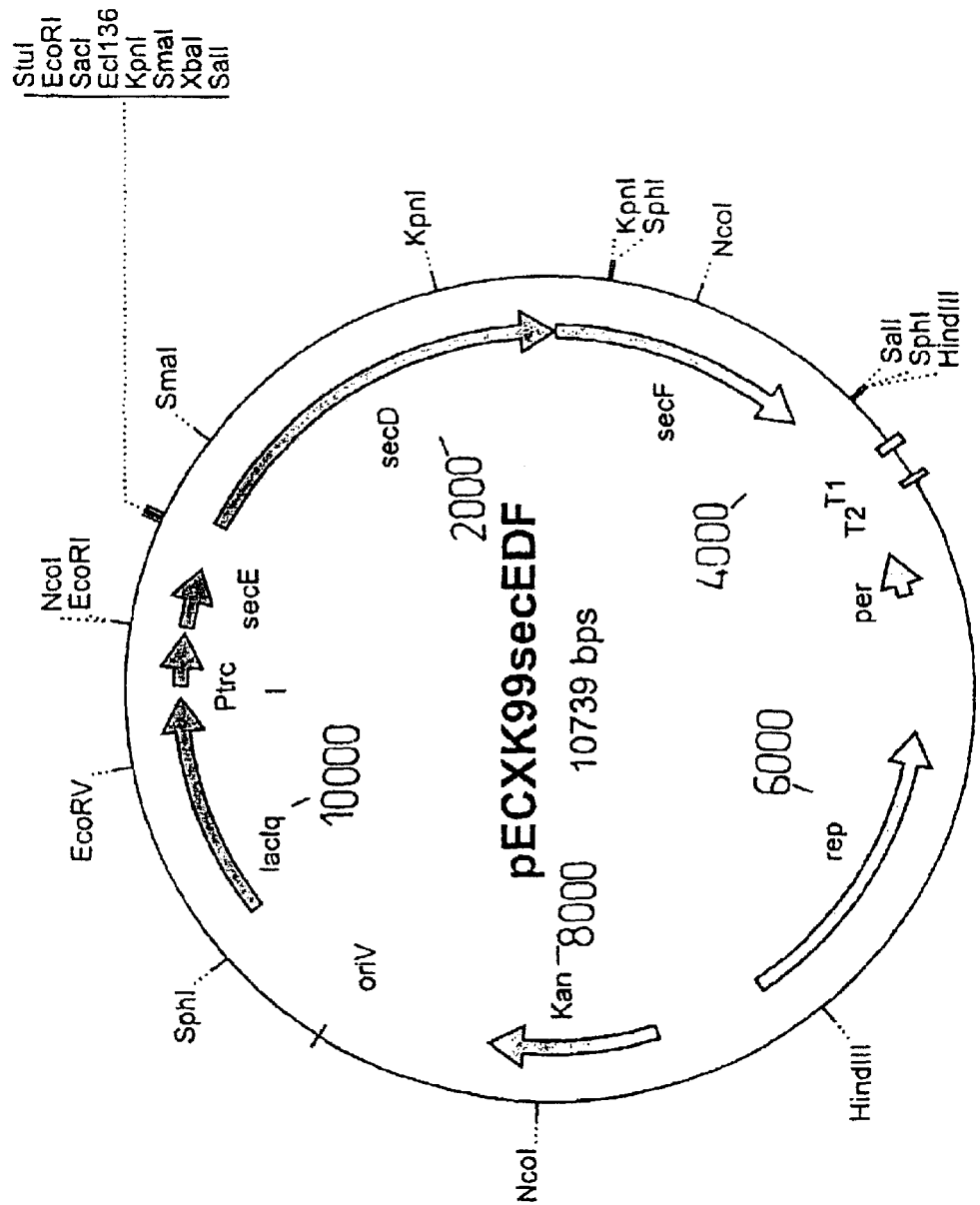
Figure 6:
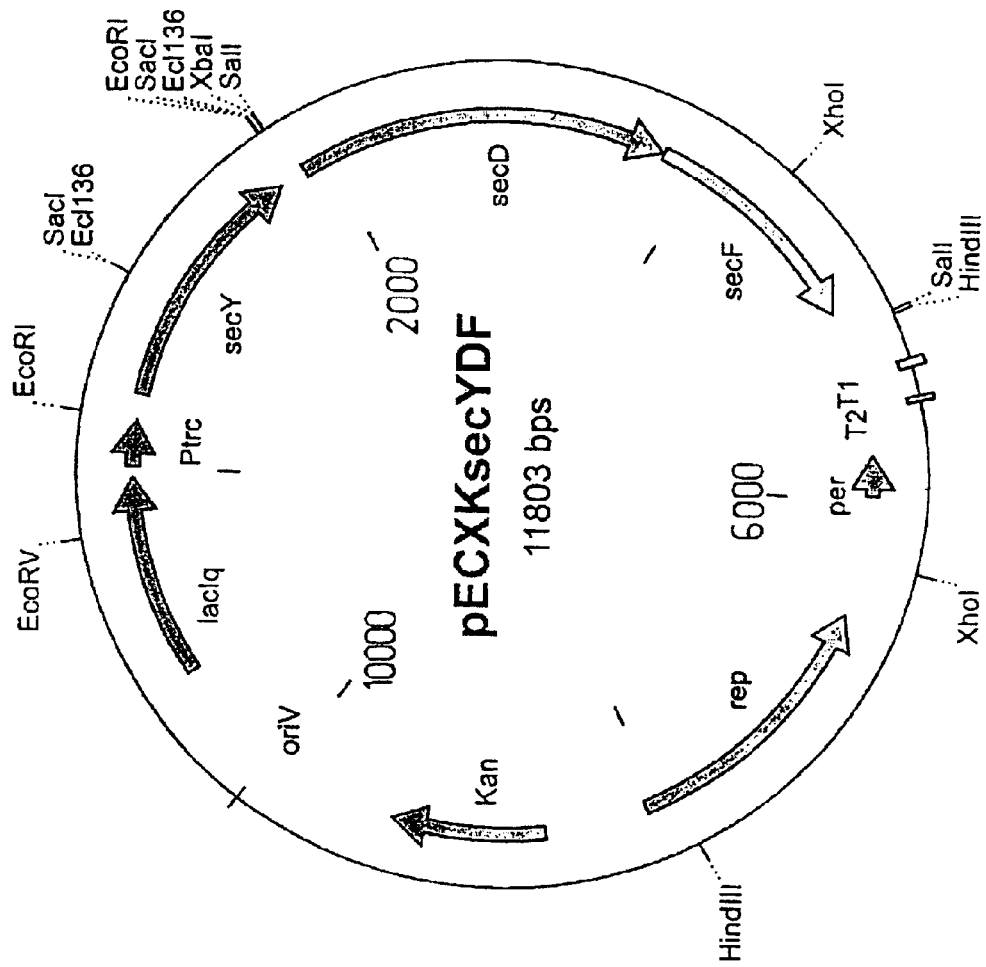
Figure 7:
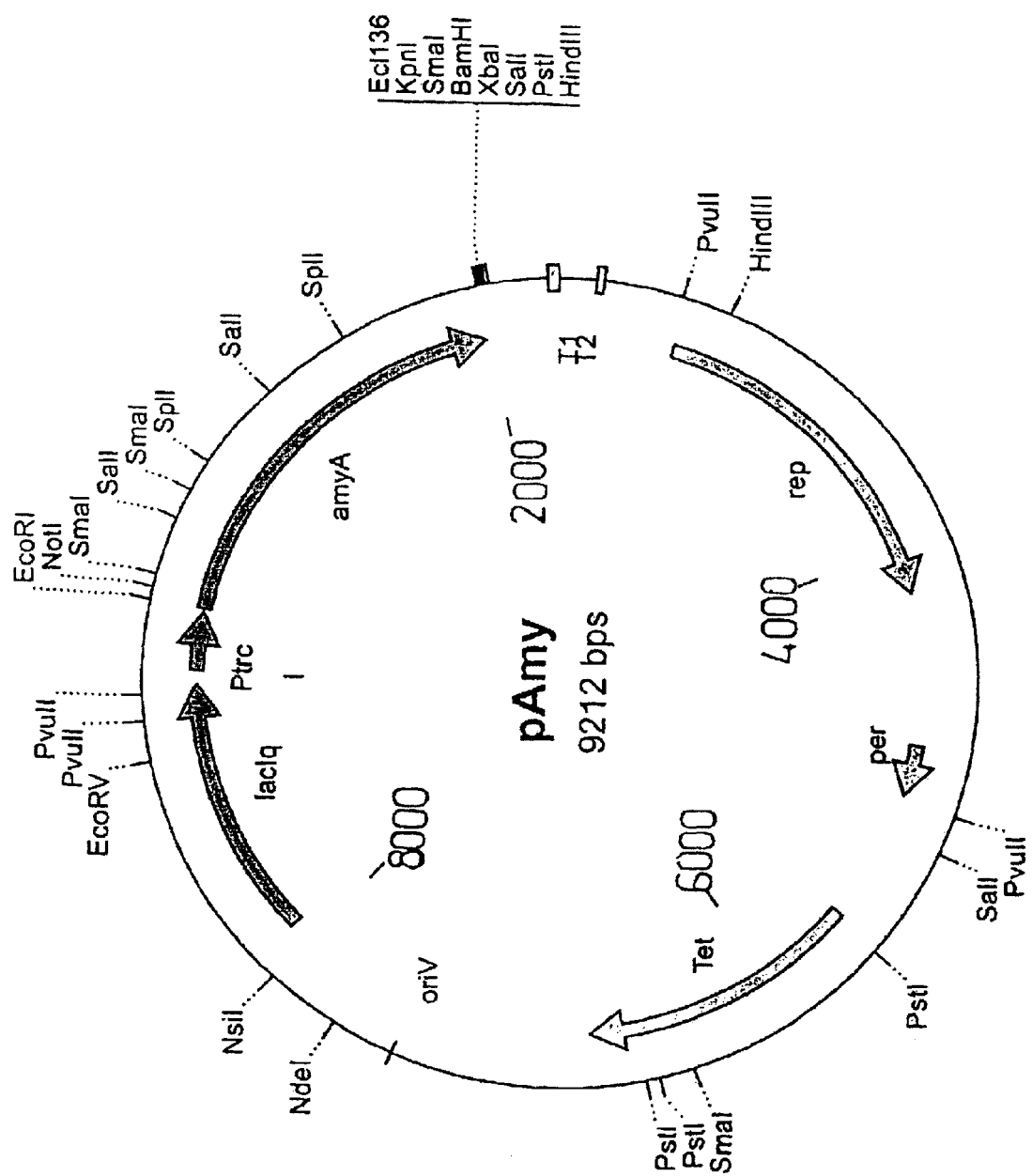
Figure 8:
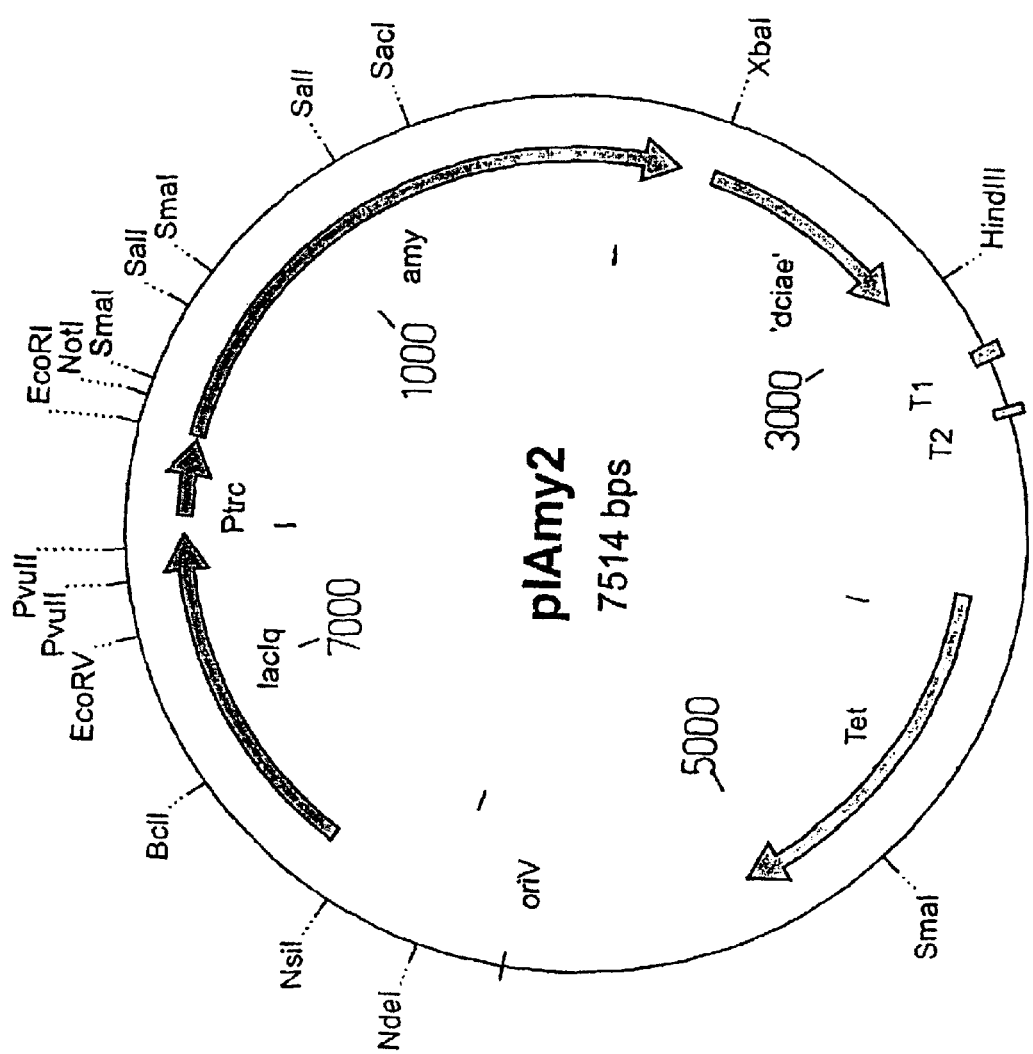

FIG. 3 is a plasmid map of pSecD
FIG. 4 is a plasmid map of pSecDF
FIG. 5 is a plasmid map of pSecEDF
FIG. 6 is a plasmid map of pSecYDF
FIG. 7 is a plasmid map of pAmy
FIG. 8 is a plasmid map of pIAmy2

The following examples shall be considered as explaining the present invention in detail without restricting the scope of the invention.

All bacterial strains and plasmids relevant for this study are listed in Table 1. *E. coli* and *Corynebacterium glutamicum* strains were routinely cultivated in Luria-Bertani (LB) medium (Sambrook, J., Fritsch, E. F., and Maniatis, T. (1989), Molecular Cloning: a Laboratory Manual, 2$^{nd}$ edn. Cold Spring Harbour, N.Y.: Cold Spring Harbour Laboratory) at 37° C. and 30° C. respectively. For growth of *Corynebacterium glutamicum* on starch as sole carbon source, a modified minimal medium (Katsumata, R, Ozaki, A., Oka, T. and Puruya, A. (1984), J. Bact. 159, 306–311), containing 2% soluble starch (Sigma) instead of glucose and yeast extract, was used. Antibiotics used for plasmid selection were kanamycin (50 μg ml$^{-1}$) and chloramphenicol (10 μg ml$^{-1}$).

EXAMPLE 1

Construction of Expression Vectors pXT99A and pEC-XK99A

*E. coli* expression vector pTRC99A (Amann et al., 1988, Gene 69: 301–315) was cleaved with BspHI and treated with Klenow fragment. Tetracycline gene from *C. glutamicum* plasmid pAG1 (GeneBank Acc.No. AF121000) was inserted instead of ampicilline gene by ligation with T4 ligase, resulting in pXT99A. Ligation mix was electroporated into *E. coli* DH5αMCR.

For construction of pEC-XK99A *E. coli—C. glutamicum* shuttle vector pTRC99A was cleaved with BspHI and treated with Klenow fragment. Ampicilline gene was replaced by kanamycine resistance gene of *E. coli* plasmid pBSL15 (Alexeyev, M., 1995, Biotechniques 18: 52–56). Ligation and electroporation was carried out as described above. Thus plasmid pXK99A was obtained.

From plasmid pGA1 (Sonnen et al., 1991, Gene 107; 69–74) a 3484 bp fragment containing a replicon of *C. glutamicum* was obtained by restriction with BalI and PstI. This fragment was inserted into SmaI/PstI cleaved vector pK18mob2 (Tauch et al., 1998, Archives of microbiology 169: 303–312). After religation a 839 bp fragment of the inserted replicon fragment was deleted by cleavage with BamHI/XhoI and the vector fragment was treated with Klenow fragment. After religation of the vector a 2645 bp KpnI/PstI, Klenow treated fragment, containing *C. glutamicum* minimal replicon was inserted into plasmid pXK99A, cleaved with NheI and treated with Klenow-polymerase. Ligation was carried out as described above. After electroporation into *C. glutamicum* plasmid pEC-XK99A was isolated and verfied.

EXAMPLE 2

Isolation and Characterization of Corynebacterial Sec Genes

*E. coli* DH5αMCR (Grant, S. G. N., Jessee, J., Bloom, F. R. and Hanahan, D. (1990), Proc. Natl. Acad. Sci. USA 87, 4645–4649) was used as host for plasmid construction. Plasmid DNA from *E. coli* was prepared by an alkaline lysis method (Sambrook, J., Fritsch, E. F. and Maniatis, T. (1989), Moleculare Cloning: a Laboratory Manual. 2$^{nd}$ edn. Cold Spring Harbour, N.Y.: Cold Spring Harbour Laboratory) modified for *Corynebacterium glutamicum* by using 20 mg of Lysozyme ml$^{-1}$ of lysis buffer HB1 at 37° C. for 2 h. Chromosomal DNA of *Corynebacterium glutamicum* was isolated as described by Tauch, A., Kirchner, O., Wehmeier, L., Kalinowski, J. and Pühler, A (1994), FEMS Microbiol Lett. 123, 343–347. DNA restriction, agarose gel electrophoresis, Klenow treatment and ligation were carried out according to standard procedures (Sambrook et al., 1989, above). Enzymes for DNA manipulation were obtained from Pharmacia or Boehringer and used as recommended by the manufacturer. Isolation of DNA restriction fragments from agarose gels was performed by means of the Nucleotrap Extraction Kit for Nucleic Acids (Macherey-Nagel).

All primer sets used for PCR experiments are listed in Table 2. To isolate a promoterless secY, the gene was generated by PCR with synthetic oligonucleotides sy1 and sy2 (Table 2), deduced from the GenBank entree D14162. The small genes secE (GenBank AF130462) and secG (231 bps, GenBank AJ007732) were directly amplified from the chromosome using the primers se1 and se2 to receive secE and sg1 and sg2 to get secG. All PCR generated genes were first cloned into pCR2.1 using the TA Cloning Kit (Invitrogen), EcoRI digested and cloned into the IPTG inducible *E. coli/Corynebacterium glutamicum* shuttle expression vector pEC-XT99A under control of the trc promoter in a second step, resulting in the plasmids, pSecY, pSecE and pSecG.

A promoterless secD was amplified by PCR using the deduced primers sd1 and sd2, derived from the sequence of the plasmid rescue and cloned as described above.

PCR was carried out with a PCT-100 Thermocycler (MJ Research, Inc.) with a Taq DNA polymerase (Gibco-BRL). The initial denaturation was conducted at 94° C. for 2 min followed by 90 s of denaturation, 90 s of annealing at the primer dependent temperature $T_m$ (2AT+4GC) of −5° C. (Suggs, S. V., Hirose, T., Miyake, T., Kawahima, E. H., Johnson, M. L., Itakura, K. and Wallace, R. B. (1981), Developmental biology using purified genes. Academic Press, Inc., New York, N.Y., pp. 683–693), and 90 s of extension at 72° C. This cycle was repeated 32 times and completed by an extension step for 10 min at 72° C.

Plasmids were introduced in *E. coli* and *Corynebacterium glutamicum* by electroporation (Tauch et al., 1994, FEMS Microbiol. Lett. 123, 343–347; Haynes and Britz, 1989, FEMS Microbiol. Lett. 61 329–334)

DNA sequencing was done by the Institut für Innovationstransfer GmbH (Bielefeld). Searches for amino acid similarities were carried out with the BLAST service (Altschul, S. F., Gish, W., Miller, W., Myers, E. W. and Lipman, D. J. (1990), J. Mol. Biol. 125, 403–410), protein alignments were computed by the CLUSTAL W program (Thompson, J. D., Higgins, D. G. and Gibson, T. J., (1994), Nucleic Acid Res. 22, 4673–4680).

In the *Mycobacterium tuberculosis* H37Rv strain, that is taxonomically closely related to *Corynebacterium glutamicum*, the dipeptid transporter encoding gene dciAE is located downstream of secD and secF. The dciAE homolog of *Corynebacterium glutamicum* (ATCC 13032) was sequenced in part in a study on the rel gene (Wehmeier, L. Schäfer, A., Burkowski, A., Krämer, R., Mechold, U., Malke, H., Pühler, A. und Kalinowski, J. (1998), Microbiology 144, 1853–1862) to isolate the genes secD and secF by a chromosomal rescue technique, an 0.8 kb fragment of the dciAE gene, derived from plasmid pLW60 (Wehmeier et al., 1998) by digestion with EcoRI and BamHI was cloned into pCR2.1 and the resulting plasmid was integrated into the *Corynebacterium glutamicum* chromosome after electoporation via homologous recombination. Total chromosomal DNA was isolated from the resulting strain, digested with EcoRV and SspI religated and transferred to *E.coli*DH5αMCR. The rescue of the integrated vector with EcoRV and SspI results in a plasmid pCR2.1 carrying a 9751 bp insert including dciAE and the upstream chromosomal region. The insert was sequenced by primer walking. By DNA sequence analysis, 8 complete and 1 partial orfs ("open reading frames"), including secD and secF could be identified on the fragment.

Sequences of secD and secF are shown as SEQ ID NO. 1 and SEQ ID NO. 2, respectively.

hybridisation. A secF mutant strain *Corynebacterium glutamicum* INT-F was build in the same way, using the primers sff1 and sff2 to reveal an internal fragment of 603 bp (nt 346–949), leading to the plasmid pInsF. For secA and secY mutation, internal fragments of the genes, derived by PCR using the primers saf1, saf2, syf1 and syf2 respectively, were cloned into pCR2.1 but failed to integrate into the chromosome.

TABLE 2

PCR primers for amplifying corynebacterial sec genes

| Gene | 5'-primer | 3'-primer |
| --- | --- | --- |
| secA fragment | saf1: 5'-CGCGACAAGGACTACATCGT-3' (SEQ ID NO:5) | saf2: 5'-GAGATGTCTGCGGATTCGAG-3' (SEQ ID NO:15) |
| secY fragment | syf1: 5'-TGAGGAGGCCAGGAGGCCAG-3' (SEQ ID NO:6) | syf2: 5'-AACCACCGTACTGACGACGA-3' (SEQ ID NO:16) |
| secY | sy1: 5'-TTAAGTGCTGAGGAGGCCAG-3' (SEQ ID NO:7) | sy2: 5'-TTATCAGCACCGGTAGTTCC-3' (SEQ ID NO:17) |
| secE | se1: 5'-TGGATGAGTAGTGATTTAGA-3' (SEQ ID NO:8) | se2: 5'-GATTCTGACTCCGTAGGTAG-3' (SEQ ID NO:18) |
| secE region | ser1: 5'-CACCTGGCAGACGCACTCAA-3' (SEQ ID NO:9) | ser2: 5'-AGCCGGAGTAGCACTGAATG-3' (SEQ ID NO:19) |
| secG | sg1: 5'-ACCTGGGTTCTCAAACGGCA-3' (SEQ ID NO:10) | sg2: 5'-TTGTCGACCTGTTGTCTCCC-3' (SEQ ID NO:20) |
| secG region | sgr1: 5'-TCCAGGCCTTGGTCACGCAA-3' (SEQ ID NO:11) | sgr2: 5'-AGCTGCGAGAATCGAGGCTA-3' (SEQ ID NO:21) |
| secD | sd1: 5'-TTGTCTGGTTGATTGGMTT-3' (SEQ ID NO:12) | sd2: 5'-TGMGTTTCAGTCTGGGMT-3' (SEQ ID NO:22) |
| secD fragment | sdf1: 5'-TGCTGTTGACAGGCGATCGT-3' (SEQ ID NO:13) | sdf2: 5'-TCATCAGTGGTGCACTGCAT-3' (SEQ ID NO:23) |
| seeF fragment | sff1: 5'-GTACCAAGATGAGCATGCCA-3' (SEQ ID NO:14) | sff2: 5'-ATCGAACGCATGAAGGTCTG-3' (SEQ ID NO:24) |

EXAMPLE 3

Construction of Plasmids pSecDF, pSecEDF and pSecYDF

The plasmid pCR2.1, carrying chromosomal secD and secF genes on a 9751 bp insert (example 1) was cleaved with SalI and a 3275 bp fragment was isolated by gel electrophoration. This fragment was inserted into pEC-XK99A, cleaved by SalI, resulting in plasmid pSecDF. Ligation and electroporation in *E. coli* DH5αMCR was carried out as described above, bacteria are incubated on LB agar plates containing 50 μg/ml kanamycine.

For construction of pSecEDF and pSecYDF, respectively, pSecDF was cleaved with EcoRI. pSecE and pSecY (example 2), respectively, were also cleaved with EcoRI, whereby the secE and secY gene containing fragments can be isolated. The EcoRI-fragments containing secE and secY genes are inserted into EcoRI-cleaved pSecDF, resulting after ligation in pSecEDF and pSecYDF, respectively.

EXAMPLE 4

Directed Mutagenesis of Sec Genes in the Chromosome of *Corynebacterium glutamicum* RES167

A defined secD mutant was constructed by gene disruption via homologous recombination. Therefore, a 609 bp internal fragment of secD (nt 1200–1809) was amplified by PCR using the deduced primers sdf1 and sdf2 (Table 2) and cloned into pCR2.1. The resulting plasmid pInsD was eletroporated into *Corynebacterium glutamicum* and could only establish itself by homologous recombination into the chromosome. The gene disruption was verified by Southern Due to the small size of secG and secE a secG mutant was constructed by insertional inactivation using the sacB system, which enables the positive selection of allelic exchanges by homologous recombination (Schäfer, A., Tauch, A., Jäger, W., Kalinowski, J., Thierbach, G. and P ühler, A. (1994), Gene 145, 69–73). For this purpose, a 1.3 kb DNA fragment with a central secG was created by PCR with the synthetic oligonucleotides sgr1 and sgr2 and subsequently cloned via pCR2.1 using SalI and XbaI into the plasmid pXT99A. To isolate the chloramphenicol resistance gene cassette cmx, vector pEC31 was digested with SalI and HindIII and the 2.0 kg fragment bearing cmx was isolated from an 0.8% agarose gel. Integration of cmx into secG was achieved by ligation of the BspHI digested plasmid and the cmx cassette after Klenow treatment of both fragments. The constructed plasmid was reisolated from *E. coli* and the 3.3 kg fragment containing secG::cmx was cloned with SalI and HindIII into pK18mobsacB (Schäfer et al., 1994). This vector pInsG was integrated into the chromosome of *Corynebacterium glutamicum* in such a way, that the resulting strain carried the modified secG region and the wild type gene separated by vector sequence. Excision of the plasmid can be selected for by growing the cells on LB agar containing 10% sucrose (Schäfer et al., 1994). Cells able to grow on this medium have lost the plasmid due to a second cross-over event that either restores wild type gene arrangements or leads to a selectable chloramphenicol resistant strain *Corynebacterium glutamicum* INT-G, carrying only the disrupted allel of secG. The secG disruption was verified by Southern hybridisation.

For disruption of secE a 1.6 kb DNA fragment was amplified by PCR using the primer ser1 and ser2, derived from the secE flanking regions (Wehmeier, 1999) and cloned via pCR2.1 into pK18mobsacB using the enzymes XbaI and HindIII. The resulting vector was cleaved at the single BssHII site within the secE gene, Klenow treated, ligated with the cmx gene fragment from pEC31 an integrated into the chromosome of *Corynebacterium glutamicum*. Further steps were carried out as described above, but no double cross-over event could be detected.

The developed mutant strains *Corynebacterium glutamicum* INT-D and *Corynebacterium glutamicum* INT-F (Table 1) are enlarged in size, showed a significantly prolonged lag phase and did not reach the optical density of the wild type in liquid media. The mutant phenotypes can be complemented by plasmid encoded, intact sec genes (not shown).

EXAMPLE 5

Construction of an Amylase Secreting Reporter System

Construction of amylase producing *Corynebacterium glutamicum* strain, the vector pULMI95 (Cadenas, R. F., Fernandez-Gonzales, C., Martin, J. F. and Gil, J. A. (1996), FEMS Microbiol. Lett. 137, 63–68) was digested with EcoRI and Ecl136II and a 2.1 kb fragment harboring the amy gene of *Streptomyces griseus* IMRU 3570 was cloned into the EcoRI and Ecl136II cleaved *E. coli*/*Corynebacterium glutamicum* shuttle expression vector pEC-XT99A under control of the IPTG-inducible trc promoter (Amman, E., Ochs, B. and Abel, K.-J. (1988), Gene 69: 301–315). The new constructed vector pAmy with IPTG inducible amylase expression was electroporated to *Corynebacterium glutamicum*.

For *Corynebacterium glutamicum* strains harbouring a chromosomal copy of the amylase gene, amy was cloned as described above into the *E. coli* expression vector pXT99A. In a second step the XbaI and HindIII gene fragment of dciAE from pLW60 (Wehmeier, et al., 1998) was cloned into the resulting vectors downstream of amy. The new non-replicative plasmid pIAmy2 was integrated into the *Corynebacterium glutamicum* chromosome by electroporation and following homologous recombination resulting in the strain *Corynebacterium glutamicum* AMY2 (Table 1).

EXAMPLE 6

Amylase Activity Assays

For performing amylase assay *Corynebacterium glutamicum* strains were cultivated in solid and liquid cultures of TYPS medium, consisting of 1% yeast extract (Difco), 1% peptone (Difco) and 2% soluble starch (Sigma). Amylase production was induced by adding 50 nM IPTG to the TYPS medium. For measurement of intracellular amylase activity, *Corynebacterium glutamicum* grown in liquid culture were washed twice in 10 mM phosphate buffer (pH 7.0). To disrupt the cells a Ribolyser (Hybaid) was used two times for 30 s at a speed of 6.

Amylase activity was measured by a modification of the dinitrosalicylic acid method (Miller, G. L., 1959, Anal. Chem. 31, 426–428) in the supernatant of *Corynebacterium glutamicum* strains. The assay was carried out at 37° C. for 30 min with 2% soluble starch in 10 mM phosphate buffer (pH 7.0). The volume activity (mU) was defined as nmol reducing sugar $min^{-1}$ $ml^{-1}$. Starch degradation was assayed on agar plates by colouring with Lugols solution. Amylase activity was detected as clearing zones around the colonies.

Starch degradation on agar plates was detectable for *Corynebacterium glutamicum* AMY2 and amylase activity in the culture supernatant after three days of incubation was 45 mU. *Corynebacterium glutamicum* AMY2, bearing a chromosomal copy of amy, secrets only 12% of the amylase produced by *Corynebacterium glutamicum* RES1167/pAmy. This led to the conclusion, that the plasmid pAmy has around 8 copies per cell in *Corynebacterium glutamicum*. In opposite to the wild type strain, all amylase producing *Corynebacterium glutamicum* strains are able to grow on minimal media with starch as only carbon source. It was concluded that amylase production is easy to assay in both, a replicative and an integrated system in *Corynebacterium glutamicum*, a sufficient reporter for protein secretion.

EXAMPLE 7

Mutation Within the GSP Diminish or Abolish Amylase Secretion

To quantify the effects of the mutations on protein export, the strains *Corynebacterium glutamicum* INT-D and *Corynebacterium glutamicum* INT-F were transformed with the replicative plasmid pAmy. Starch degradation was tested on solid medium and in liquid culture. No secretion is detectable in *Corynebacterium glutamicum* INT-D/pAmy and *Corynebacterium glutamicum* INT-F/pAmy. Determination of volume activity resembles the same phenotype no starch degradation could be found for both strains.

Due to the surprising fact of a complete loss of the ability to secrete the heterologous amylase, the other sec genes of *Corynebacterium glutamicum* were mutated. Producing mutants of secA, secY and secE failed which are essential for cell viability, as pointed out above. To mutate secG, the wild type gene was replaced by a secG disrupted with the choramphenicol resistance cassette cmx via double cross-over using the sacB system. The resulting mutant strain *Corynebacterium glutamicum* INT-G (Table 1) grows normal at permissive temperatures but its cell wall is very sensitive against SDS (data not shown). All mutation were verified by Southern hybridisation.

Like the strains *Corynebacterium glutamicum* INT-D and *Corynebacterium glutamicum* INT-F, *Corynebacterium glutamicum* INT-G was transformed with the replicative plasmid pAmy to analyse the effect of the gene disruption on the protein export. Starch degradation was tested on solid medium and in liquid culture. Amylase secretion is significantly diminished in *Corynebacterium glutamicum* INT-G/pAmy, compared with *Corynebacterium glutamicum* RES167/pAmy: The mutant strain secrets only 21.5% of the amylase exported by *Corynebacterium glutamicum* RES167/pAmy.

None of the strains showed any amylase activity in the cytoplasma. Due to this, we conclude that an intact secD and secF are inevitable for the export of the heterologous amylase. SecG is not essential for protein translocation itself but strongly influences the rate of export.

EXAMPLE 8

Overexpression of Combination of Sec Genes Increases Amylase Secretion

Since SecD and SecF seems to be strong effectors on amylase secretion, the consequence of combined overexpression of secD and secF on protein export was examined. The combination secD and secF was cloned with SalI into the shuttle expression vector pEC-XK99A as described above. *Corynebacterium glutamicum* AMY2 was transformed with the resulting plasmids pSecDF and tested for amylase activity. As pointed out in FIG. 1, the simultaneous overexpression of secD and secF genes enhanced the amylase secretion 1.5 fold in contrast to *Corynebacterium glutamicum* AMY2.

Figure 1:
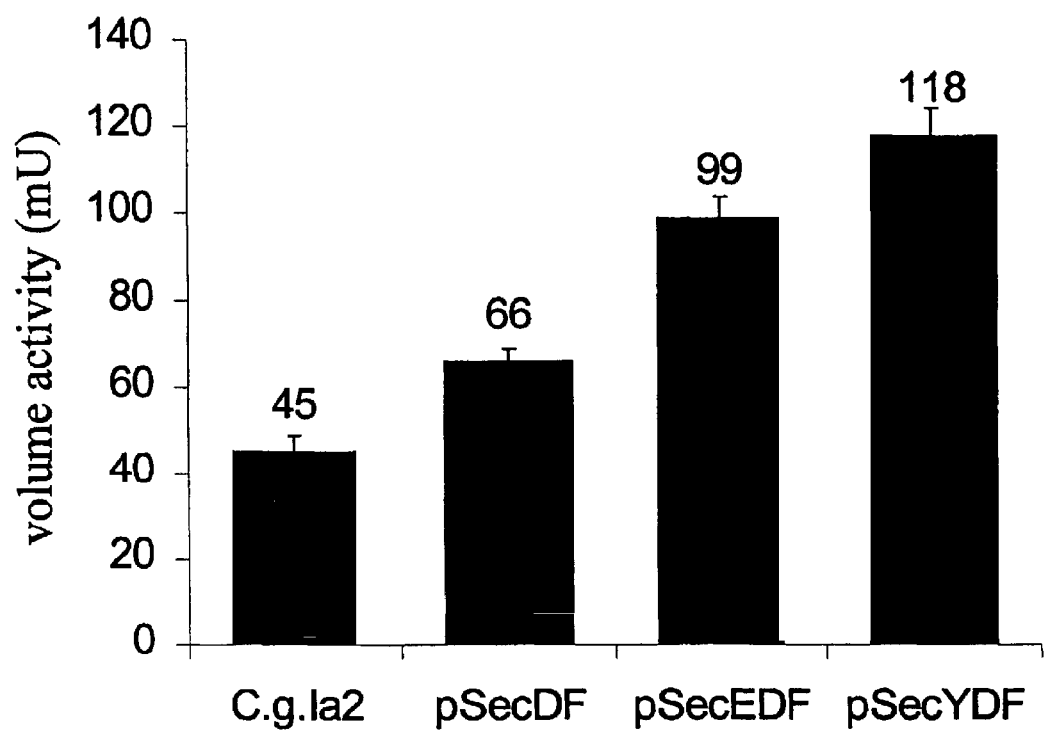
FIG. 1
Figure 2:
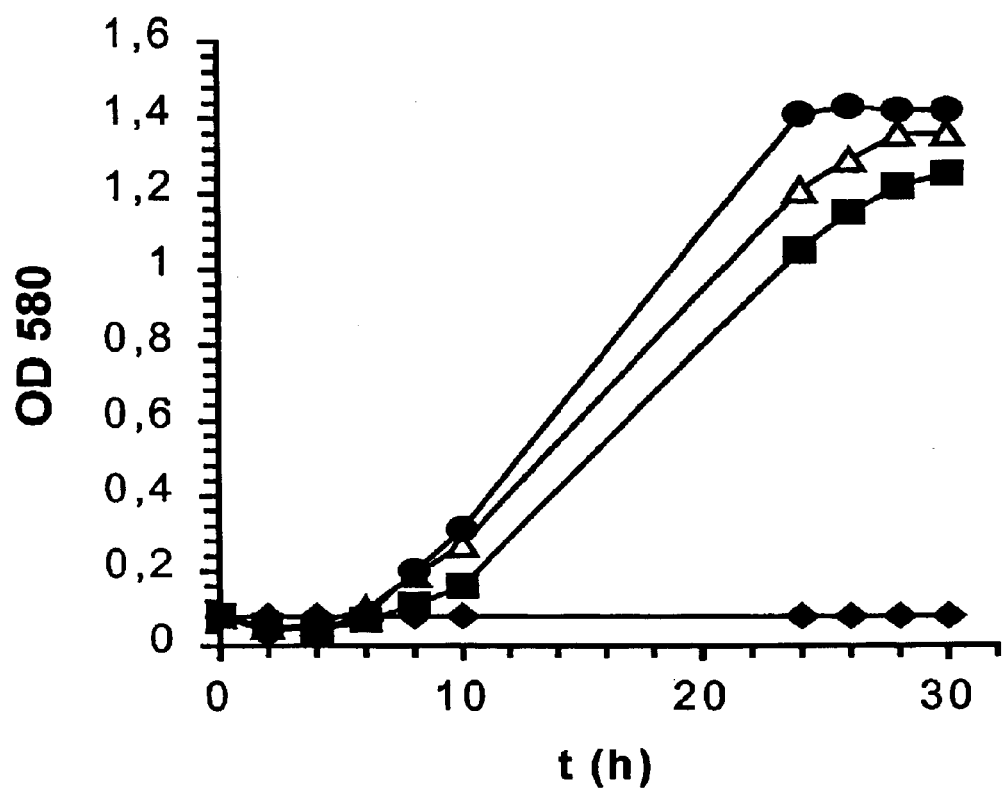

To analyze the effect of parallel overexpression of auxiliary sec genes secD and secF with essential sec genes, secE and secY EcoRI were cloned into pSecDF, resulting in the plasmids pSecEDF and pSecYDF as described in example 3. SecE and SecY were cloned, because their interaction with the SecD/SecF complex is described in *E. coli* (Sagara, K., Matsujama, S. and Mitzushima, S., 1994, J. Bact. 176, 4111–4116). Test on amylase secretion revealed a 2.3 fold increase for *Corynebacterium glutamicum* AMY2/pSecEDF and gained 2.5 fold for *Corynebacterium glutamicum* AMY2/pSecYDF compared with *Corynebacterium glutamicum* AMY2 (FIG. 1).

Detection of amylase activity on solid medium indicates the same findings. After 24 h the starch degradation was more progressed for *Corynebacterium glutamicum* AMY2/pSecEDF and *Corynebacterium glutamicum* AMY2/pSecYDF have higher doubling rates than *Corynebacterium glutamicum* AMY2.

Growth in minimal medium with starch as sole carbon source mirrored these results: No growth is detectable for *Corynebacterium glutamicum* RES167 due to its inability to convert starch to a metabolizable form. *Corynebacterium glutamicum* AMY2/pSecEDF and *Corynebacterium glutamicum* AMY2/pSecYDF, which revealed the highest amylase secretion, showed the fastest growth of all tested strains and reached a slightly higher OD. This indicates that growth on starch is directly proportional to amylase secretion.

What is claimed is:

1. A recombinant *Corynebacterium glutamicum* bacterium transformed with at least one isolated *Corynebacterium glutamicum* polynucleotide selected from the group consisting of:
   a) an isolated polynucleotide encoding a polypeptide comprising the amino acid sequence of SEQ ID NO:3; and
   b) an isolated polynucleotide encoding a polypeptide comprising the amino acid sequence of SEQ ID NO:4.

2. The bacterium of claim 1, wherein said polypeptide comprising the amino acid sequence of SEQ ID NO: 3 enhances excretion of an α-amylase from the cytoplasm of said bacterium to a broth as compared to a non-transformed wild-type *Corynebacterium glutamicum* bacterium.

3. The bacterium of claim 1, wherein said polypeptide comprising the amino acid sequence of SEQ ID NO: 4 enhances excretion of an α-amylase from the cytoplasm of said bacterium to a broth as compared to a non-transformed wild-type *Corynebacterium glutamicum* bacterium.

4. A recombinant *Corynebacterium glutamicum* bacterium transformed with at least one *Corynebacterium glutamicum* polynucleotide selected from the group consisting of:
   a) an isolated polynucleotide comprising nucleotides 34 to 944 of SEQ ID NO:1; and
   b) an isolated polynucleotide comprising nucleotides 22 to 1230 of SEQ ID NO:2.

5. The bacterium of claim 4, wherein said isolated polynucleotide comprising nucleotides 34 to 1944 of SEQ ID NO: 1 encodes a polypeptide that enhances excretion of an α-amylase from the cytoplasm of said bacterium to a broth as compared to a non-transformed wild-type *Corynebacterium glutamicum* bacterium.

6. The bacterium of claim 4, wherein said isolated polynucleotide comprising nucleotides 22 to 1230 of SEQ ID NO: 2 encodes a polypeptide that enhances excretion of an α-amylase from the cytoplasm of said bacterium to a broth as compared to a non-transformed wild-type *Corynebacterium glutamicum* bacterium.

7. The bacterium of claim 1 wherein said isolated polynucleotide encoding said polypeptide is overexpressed.

8. The bacterium of claims 5 or 6 wherein said isolated polynucleotide encoding said polypeptide is overexpressed.

9. A vector comprising an isolated polynucleotide as set forth in any of claims 1 or 4.

10. The bacterium of any of the claims 1 or 4, whereby in said bacterium at least one polypeptide selected from the group consisting of the secretory polypeptide SecE encoded by the secE gene native to *Corynebacterium glutamicum*, the secretory polypeptide SecY encoded by the secY gene native to *Corynebacterium glutamicum* and the secretory polypeptide SecA encoded by the secA gene native to *Corynebacterium glutamicum* is overexpressed.

11. The bacterium of any of the claims 1 or 4, wherein said bacterium further comprises a nucleic acid encoding a heterologous polypeptide.

12. The bacterium of claim 11, wherein said nucleic acid encoding a heterologous polypeptide is selected from the group consisting of a nucleic acid encoding a cellulase, a nucleic acid encoding an interferon, a nucleic acid encoding a lipase, and a nucleic acid encoding a nuclease.

13. The bacterium of claim 11, wherein said nucleic acid encoding a heterologous polypeptide is a nucleic acid encoding a cellulase.

14. The bacterium of claim 11, wherein said nucleic acid encoding a heterologous polypeptide is a nucleic acid encoding an amylase.

15. The bacterium of claim 14, wherein said nucleic acid encoding an amylase is a nucleic acid to the genus *Streptomyces*.

16. The bacterium of claim 15, wherein said nucleic acid of the genus *Streptomyces* is native to the species *Streptomyces griseus*.

17. A recombinant *Corynebacterium glutamicum* transformed with a *Corynebacterium glutamicum* nucleic acid consisting of SEQ ID NO: 1 or a fragment thereof, and encoding a polypeptide that enhances excretion of an α-amylase from the cytoplasm of said bacterium to a broth as compared to a non-transformed wild-type *Corynebacterium glutamicum* bacterium.

18. A recombinant *Corynebacterium glutamicum* transformed with a *Corynebacterium glutamicum* nucleic acid consisting of SEQ ID NO: 2 or a fragment thereof, and encoding a polypeptide that enhances excretion of an α-amylase from the cytoplasm of said bacterium to a broth as compared to a non-transformed wild-type *Corynebacterium glutamicum* bacterium.

19. A vector comprising the nucleic acid molecule of claims 17 or 18.

20. A host cell transformed with the vector of claim 19.

* * * * *

UNITED STATES PATENT AND TRADEMARK OFFICE
CERTIFICATE OF CORRECTION

PATENT NO. : 6,982,162 B2
DATED : January 3, 2006
INVENTOR(S) : Stephen Berens et al.

It is certified that error appears in the above-identified patent and that said Letters Patent is hereby corrected as shown below:

<u>Title page,</u>
Item [73], Assignee, replace "Dusselforf" with -- Dusseldorf --.

<u>Column 29,</u>
Line 26, replace "944" with -- 1944 --.

Signed and Sealed this

Thirtieth Day of May, 2006

JON W. DUDAS
*Director of the United States Patent and Trademark Office*

SEQUENCE LISTING

<160> NUMBER OF SEQ ID NOS: 24

<210> SEQ ID NO 1
<211> LENGTH: 1960
<212> TYPE: DNA
<213> ORGANISM: Corynebacterium glutamicum
<220> FEATURE:
<221> NAME/KEY: misc_feature
<222> LOCATION: (34)..(1944)
<223> OTHER INFORMATION: secD

<400> SEQUENCE: 1

```
ttgtctggtt gattggaatt gaaggagact ttcttggctc ggcaaaaaaa gagtgccgct      60
agcgcctggg aacgatggcc aaaacgcgca atagcgttgt ttgtgctcat cgtcgttggt     120
gtttatgcgt tggtgctgtt gacaggcgat cgttctgcca caccaaaatt gggtattgat     180
ctgcaaggcg aacccgagt gaccctcgtg ccgcagggc aggatccaac tcaggaccag      240
ctgaatcagg cacgcaccat tctggaaaac cgtgtgaacg gcatgggcgt ttcaggtgca     300
agcgtggtcg ctgacggtaa cacgctggtg atcactgttc ccggggaaaa taccgcacag     360
gcgcaatccc taggacagac ctcccagctg ctgttccgtc ccgttggtca ggcaggaatg     420
cccgatatga ccacgttgat gccagagctg gaagagatgg ccaacaggtg ggttgaatac     480
ggcgtcatca ccgaagagca ggcaaatgcc tccttggagg aaatgaacac cgctgttgca     540
tcgaccactg cggtggaagg cgaagaagca actgagccag aacccgtcac cgtgtcggcg     600 accctatgg atgagccagc caactccatt gaggcaacac agcgacgcca ggaaatcacg     660
gacatgctgc gcaccgaccg ccagtccacc gatcccactg tccagatcgc tgcaagttct     720
ttgatgcagt gcaccactga tgagatggat cctttggccg gcaccgatga tccacgcctg     780
ccattggtgg catgtgatcc agctgtaggt ggcgtgtatg tacttgatcc tgcacctttg     840
ctcaacggcg aaaccgatga ggaaaatggt gcgcgcctaa ccggtaatga gatcgatacc     900
aaccgtccca tcaccggtgg attcaacgcc cagtccggcc agatggaaat cagctttgcc     960
ttcaaatccg gcgatgggga agaaggctct gcaacttggt cctctctgac cagccagtac    1020
ctgcagcagc agatcgccat caccctggac tctcaggtga tttctgcacc cgtgattcag    1080
tcagcaaccc ctgtgggttc tgcaacatcc atcaccggtg acttcactca aactgaagcc    1140
caagatctgg cgaacaacct gcgctacggt gcattgcccc tgagcttcgc aggtgaaaac    1200
ggcgagcgcg gcggaactac caccaccgtt ccgccatcac taggcgcagc atccttgaag    1260
```

| | |
|---|---|
| gccggactga tcgcaggcat cgtcggcatc gcgctggtcg ccatcttcgt gttcgcctac | 1320 |
| taccgcgtct tcggattcgt ttccctgttc accctgtttg ccgcaggcgt gttggtctac | 1380 |
| ggccttctgg tactgctggg acgctggatc ggatattccc tagaccttgc tggtatcgcc | 1440 |
| ggtttgatca tcggtatcgg taccaccgcc gactccttcg tggtgttcta tgagcgcatc | 1500 |
| aaggatgaga tccgtgaagg aagatccttt agatctgcag tacctcgtgc atgggaaagc | 1560 |
| gccaagcgca ccatcgtcac aggcaacatg gtcactttgc tcggcgctat cgtgatttac | 1620 |
| ttgctcgcgg tcggcgaagt caagggcttt gccttcaccc tgggtctgac caccgtattc | 1680 |
| gatctcgttg tcaccttcct gatcacggca ccactggtta tcctggcatc acgcaaccca | 1740 |
| ttctttgcca agtcatcggt caacggcatg gacgagtga tgaagctcgt tgaagaacgc | 1800 |
| cgcgccaacg gtgaattgga tgagcctgag tacctgaaaa agatccatgc caagaatgcg | 1860 |
| gcagctgata aggcttccac tgacaattct tccactgaca attctgaagc acctggcacc | 1920 |
| gatacgaacc aagaggagga gaagtagcca tgactgattc | 1960 |

<210> SEQ ID NO 2
<211> LENGTH: 1562
<212> TYPE: DNA
<213> ORGANISM: Corynebacterium glutamicum
<220> FEATURE:
<221> NAME/KEY: misc_feature
<222> LOCATION: (22)..(1230)
<223> OTHER INFORMATION: secF

<400> SEQUENCE: 2

| | |
|---|---|
| ccaagaggag gagaagtagc catgactgat tcccagactg aatcactgtc aactcagagc | 60 |
| gtaaaaccag ccaaaaaacg cagttggttc aacagcctct acaccggtga cggcggcatt | 120 |
| gacttcatcg ccaaaaccaa actgtggtac tggatcaccg gcattttgct ggttatctcg | 180 |
| atcctgttca tcgccatccg tggcttctcc ctgagcatcg atttccaggg cggtaccaag | 240 |
| atgagcatgc cagcatcgga ttactccacc gaacaggtgg aggaaacctt tactgaagcc | 300 |
| accggcatta ctccggaaat cgtgcagatc gtcggttccg cgacgcccg caccctggag | 360 |
| atctactccg agcgactcag cgatgaggat gtagaaaaag cccgcctggc gatctacgag | 420 |
| gaataccaac ccctaaactc tgagggccag ccaagcccag atgccatcgg taattccacg | 480 |
| gtgtcggaat catggggttc caccatcacc caacgcatgg tgttggctct gattgccttc | 540 |
| ctggttattg cagcgatcta cattgctttc cgcctcgagc gtgaaatggc catcgccgcc | 600 |
| atggcagcat tggttgttga cggcatcgtc atcgccggca tctacgccgt catcggcctc | 660 |
| gaagtatccc cagcaaccgt catcggtctg ctcaccgtgc tgaccttctc catctacgac | 720 |
| accgtcgtgg tctttgacaa ggtcagagaa acaccgaag gcttcgaagg cagccgcaga | 780 |
| cgaacctacg ccgaacaagc caacctggcg gtcaaccaga ccttcatgcg ttcgatctcc | 840 |
| acgacaatca tctctgcact tccgatcatc gctttgatgt tgtcgccgt ctggatgatg | 900 |
| ggtgttggca ccctcaaaga cctcgcactg atccagctga tcggcgtcat cgaaggcacc | 960 |
| ttctcctccg tcttcctggc aaccccactg ctggtcagcc tgaaaaaccg cctgagcaaa | 1020 |
| accaaagcgc acaccgcttc cgttatgaag ttgcgcgacg gccaaagcac gcttatcgac | 1080 |
| gccacccac acaccaacgc cgacgcctcc gcgcacggca ccgaaagcga cactgacggt | 1140 |
| gtgaccccg aagcacctgc aaaacgtaca gtaagcaaac ccattgtgga tgatcaccga | 1200 |
| tcaagcggaa cctggcgacc aggcagaagc taaaccaatt ggagaacgaa gaaaaatccc | 1260 |
| gcagactcgc gttctgcggg attttttttg tgcgtctatg actcacgatg ttcccaaacg | 1320 |

-continued

```
acgacttcac gtggtcgact tcagtcggat ttgccgtttt tatccagtga agtcggctca    1380
tgagaagttg agcacgcgaa gtcgtaggtt gaggtctcgt aatctgcggt gtcgtaggtt    1440
gagatgtcgc cgccttaagt tcgatttctc accttcgata cctcacgctc aatttcttat    1500
gttcgagacc gctaggaaaa gcaccaaaaa ccgactgaaa ttgagtttgg gaaattgagc    1560
gc                                                                   1562
```

```
<210> SEQ ID NO 3
<211> LENGTH: 637
<212> TYPE: PRT
<213> ORGANISM: Corynebacterium glutamicum
<220> FEATURE:
<221> NAME/KEY: PROPEP
<222> LOCATION: (1)..(637)
<223> OTHER INFORMATION: secD

<400> SEQUENCE: 3
```

Met Ala Arg Gln Lys Lys Ser Ala Ala Ser Ala Trp Glu Arg Trp Pro
 1               5                  10                  15

Lys Arg Ala Ile Ala Leu Phe Val Leu Ile Val Val Gly Val Tyr Ala
            20                  25                  30

Leu Val Leu Leu Thr Gly Asp Arg Ser Ala Thr Pro Lys Leu Gly Ile
        35                  40                  45

Asp Leu Gln Gly Gly Thr Arg Val Thr Leu Val Pro Gln Gly Gln Asp
    50                  55                  60

Pro Thr Gln Asp Gln Leu Asn Gln Ala Arg Thr Ile Leu Glu Asn Arg
65                  70                  75                  80

Val Asn Gly Met Gly Val Ser Gly Ala Ser Val Ala Asp Gly Asn
            85                  90                  95

Thr Leu Val Ile Thr Val Pro Gly Glu Asn Thr Ala Gln Ala Gln Ser
        100                 105                 110

Leu Gly Gln Thr Ser Gln Leu Leu Phe Arg Pro Val Gly Gln Ala Gly
        115                 120                 125

Met Pro Asp Met Thr Thr Leu Met Pro Glu Leu Glu Glu Met Ala Asn
    130                 135                 140

Arg Trp Val Glu Tyr Gly Val Ile Thr Glu Glu Gln Ala Asn Ala Ser
145                 150                 155                 160

Leu Glu Glu Met Asn Thr Ala Val Ala Ser Thr Thr Ala Val Glu Gly
                165                 170                 175

Glu Glu Ala Thr Glu Pro Glu Pro Val Thr Val Ser Ala Thr Pro Met
            180                 185                 190

Asp Glu Pro Ala Asn Ser Ile Glu Ala Thr Gln Arg Arg Gln Glu Ile
        195                 200                 205

Thr Asp Met Leu Arg Thr Asp Arg Gln Ser Thr Asp Pro Thr Val Gln
    210                 215                 220

Ile Ala Ala Ser Ser Leu Met Gln Cys Thr Thr Asp Glu Met Asp Pro
225                 230                 235                 240

Leu Ala Gly Thr Asp Asp Pro Arg Leu Pro Leu Val Ala Cys Asp Pro
                245                 250                 255

Ala Val Gly Gly Val Tyr Val Leu Asp Pro Ala Pro Leu Leu Asn Gly
            260                 265                 270

Glu Thr Asp Glu Glu Asn Gly Ala Arg Leu Thr Gly Asn Glu Ile Asp
        275                 280                 285

Thr Asn Arg Pro Ile Thr Gly Gly Phe Asn Ala Gln Ser Gly Gln Met
    290                 295                 300

```
Glu Ile Ser Phe Ala Phe Lys Ser Gly Asp Gly Glu Gly Ser Ala
305                 310                 315                 320

Thr Trp Ser Ser Leu Thr Ser Gln Tyr Leu Gln Gln Ile Ala Ile
            325                 330                 335

Thr Leu Asp Ser Gln Val Ile Ser Ala Pro Val Ile Gln Ser Ala Thr
            340                 345                 350

Pro Val Gly Ser Ala Thr Ser Ile Thr Gly Asp Phe Thr Gln Thr Glu
            355                 360                 365

Ala Gln Asp Leu Ala Asn Asn Leu Arg Tyr Gly Ala Leu Pro Leu Ser
370                 375                 380

Phe Ala Gly Glu Asn Gly Glu Arg Gly Gly Thr Thr Thr Val Pro
385                 390                 395                 400

Pro Ser Leu Gly Ala Ala Ser Leu Lys Ala Gly Leu Ile Ala Gly Ile
                405                 410                 415

Val Gly Ile Ala Leu Val Ala Ile Phe Val Phe Ala Tyr Tyr Arg Val
            420                 425                 430

Phe Gly Phe Val Ser Leu Phe Thr Leu Phe Ala Ala Gly Val Leu Val
            435                 440                 445

Tyr Gly Leu Leu Val Leu Leu Gly Arg Trp Ile Gly Tyr Ser Leu Asp
    450                 455                 460

Leu Ala Gly Ile Ala Gly Leu Ile Ile Gly Ile Gly Thr Thr Ala Asp
465                 470                 475                 480

Ser Phe Val Val Phe Tyr Glu Arg Ile Lys Asp Glu Ile Arg Glu Gly
                485                 490                 495

Arg Ser Phe Arg Ser Ala Val Pro Arg Ala Trp Glu Ser Ala Lys Arg
                500                 505                 510

Thr Ile Val Thr Gly Asn Met Val Thr Leu Leu Gly Ala Ile Val Ile
            515                 520                 525

Tyr Leu Leu Ala Val Gly Glu Val Lys Gly Phe Ala Phe Thr Leu Gly
    530                 535                 540

Leu Thr Thr Val Phe Asp Leu Val Val Thr Phe Leu Ile Thr Ala Pro
545                 550                 555                 560

Leu Val Ile Leu Ala Ser Arg Asn Pro Phe Phe Ala Lys Ser Ser Val
                565                 570                 575

Asn Gly Met Gly Arg Val Met Lys Leu Val Glu Glu Arg Arg Ala Asn
            580                 585                 590

Gly Glu Leu Asp Glu Pro Glu Tyr Leu Lys Lys Ile His Ala Lys Asn
        595                 600                 605

Ala Ala Ala Asp Lys Ala Ser Thr Asp Asn Ser Ser Thr Asp Asn Ser
610                 615                 620

Glu Ala Pro Gly Thr Asp Thr Asn Gln Glu Glu Lys
625                 630                 635

<210> SEQ ID NO 4
<211> LENGTH: 403
<212> TYPE: PRT
<213> ORGANISM: Corynebacterium glutamicum
<220> FEATURE:
<221> NAME/KEY: PROPEP
<222> LOCATION: (1)..(403)
<223> OTHER INFORMATION: secF

<400> SEQUENCE: 4

Met Thr Asp Ser Gln Thr Glu Ser Leu Ser Thr Gln Ser Val Lys Pro
 1               5                  10                  15
```

```
Ala Lys Lys Arg Ser Trp Phe Asn Ser Leu Tyr Thr Gly Asp Gly Gly
            20                  25                  30

Ile Asp Phe Ile Ala Lys Thr Lys Leu Trp Tyr Trp Ile Thr Gly Ile
        35                  40                  45

Leu Leu Val Ile Ser Ile Leu Phe Ile Ala Ile Arg Gly Phe Ser Leu
    50                  55                  60

Ser Ile Asp Phe Gln Gly Gly Thr Lys Met Ser Met Pro Ala Ser Asp
65                  70                  75                  80

Tyr Ser Thr Glu Gln Val Glu Thr Phe Thr Glu Ala Thr Gly Ile
                85                  90                  95

Thr Pro Glu Ile Val Gln Ile Val Gly Ser Gly Asp Ala Arg Thr Leu
                100                 105                 110

Glu Ile Tyr Ser Glu Arg Leu Ser Asp Glu Asp Val Glu Lys Ala Arg
            115                 120                 125

Leu Ala Ile Tyr Glu Glu Tyr Gln Pro Leu Asn Ser Glu Gly Gln Pro
    130                 135                 140

Ser Pro Asp Ala Ile Gly Asn Ser Thr Val Ser Glu Ser Trp Gly Ser
145                 150                 155                 160

Thr Ile Thr Gln Arg Met Val Leu Ala Leu Ile Ala Phe Leu Val Ile
                165                 170                 175

Ala Ala Ile Tyr Ile Ala Phe Arg Leu Glu Arg Glu Met Ala Ile Ala
            180                 185                 190

Ala Met Ala Ala Leu Val Val Asp Gly Ile Val Ile Ala Gly Ile Tyr
    195                 200                 205

Ala Val Ile Gly Leu Glu Val Ser Pro Ala Thr Val Ile Gly Leu Leu
    210                 215                 220

Thr Val Leu Thr Phe Ser Ile Tyr Asp Thr Val Val Phe Asp Lys
225                 230                 235                 240

Val Arg Glu Asn Thr Glu Gly Phe Glu Gly Ser Arg Arg Thr Tyr
                245                 250                 255

Ala Glu Gln Ala Asn Leu Ala Val Asn Gln Thr Phe Met Arg Ser Ile
            260                 265                 270

Ser Thr Thr Ile Ile Ser Ala Leu Pro Ile Ile Ala Leu Met Val Val
        275                 280                 285

Ala Val Trp Met Met Gly Val Gly Thr Leu Lys Asp Leu Ala Leu Ile
    290                 295                 300

Gln Leu Ile Gly Val Ile Glu Gly Thr Phe Ser Ser Val Phe Leu Ala
305                 310                 315                 320

Thr Pro Leu Leu Val Ser Leu Lys Asn Arg Leu Ser Lys Thr Lys Ala
                325                 330                 335

His Thr Ala Ser Val Met Lys Leu Arg Asp Gly Gln Ser Thr Leu Ile
            340                 345                 350

Asp Ala Thr Pro His Thr Asn Ala Asp Ala Ser Ala His Gly Thr Glu
        355                 360                 365

Ser Asp Thr Asp Gly Val Thr Pro Glu Ala Pro Ala Lys Arg Thr Val
    370                 375                 380

Ser Lys Pro Ile Val Asp Asp His Arg Ser Ser Gly Thr Trp Arg Pro
385                 390                 395                 400

Gly Arg Ser

<210> SEQ ID NO 5
<211> LENGTH: 20
<212> TYPE: DNA
<213> ORGANISM: Artificial Sequence
```

```
<220> FEATURE:
<223> OTHER INFORMATION: Description of Artificial Sequence: Primer

<400> SEQUENCE: 5
cgcgacaagg actacatcgt                                              20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 6
tgaggaggcc aggaggccag                                              20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 7
ttaagtgctg aggaggccag                                              20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 8
tggatgagta gtgatttaga                                              20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 9
cacctggcag acgcactcaa                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 10
acctgggttc tcaaacggca                                              20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 11
tccaggcctt cctcacgcaa                                              20
```

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 12
ttgtctggtt gattggaatt                                                 20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 13
tgctgttgac aggcgatcgt                                                 20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 14
gtaccaagat gagcatgcca                                                 20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 15
gagatgtctg cggattcgag                                                 20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 16
aaccaccgta ctgacgacga                                                 20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 17
ttatcagcac cggtagttcc                                                 20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Primer

```
<400> SEQUENCE: 18
gattctgact ccgtaggtag                                            20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 19
agccggagta gcactgaatg                                            20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 20
ttgtcgacct gttgtctccc                                            20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 21
agctgcgaga atccaggcta                                            20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 22
tgaagtttca gtctgggaat                                            20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 23
tcatcagtgg tgcactgcat                                            20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 24
atcgaacgca tgaaggtctg                                            20
```